United States Patent [19]

Nestrick et al.

[11] 4,376,641
[45] Mar. 15, 1983

[54] COATED CAPILLARY CHROMATOGRAPHIC COLUMN

[75] Inventors: Terry J. Nestrick; Thomas L. Peters; Lester L. Lamparski, all of Midland, Mich.

[73] Assignee: The Dow Chemical Company, Midland, Mich.

[21] Appl. No.: 330,343

[22] Filed: Dec. 14, 1981

[51] Int. Cl.³ ............................................. B01D 15/08
[52] U.S. Cl. ........................................ 55/67; 55/386; 65/30.1; 65/31; 210/198.2
[58] Field of Search ................... 55/386, 67; 210/635, 210/198.2; 65/30.1, 31

[56] References Cited

U.S. PATENT DOCUMENTS

| 3,514,925 | 6/1970 | Bossart | 55/386 |
| 3,958,073 | 5/1976 | Taevisan | 65/30.1 X |
| 4,169,790 | 10/1979 | Pretorius et al. | 65/31 X |
| 4,242,227 | 12/1980 | Nestrick et al. | 252/428 |
| 4,293,415 | 10/1981 | Bente et al. | 55/386 X |

OTHER PUBLICATIONS

Milton L. Lee et al., J. of Chrom. (1980), pp. 235–312.
Bob W. Wright et al., J. of Chrom., 199 (1980), pp. 355–369.
M. Godefroot et al., "High Temperature Silylation of Glass Capillary Columns, J. of HRC & CC, Jul. 1980, pp. 337–344.
K. Grob et al., J. of HRC & CC, vol. 3, Apr. 1980, pp. 197–198, and vol. 2, Nov. 1979, pp. 677 & 678.

Primary Examiner—John Adee
Attorney, Agent, or Firm—Burke M. Halldorson

[57] ABSTRACT

In the production of a wall coated open tubular capillary chromatographic column, improved deactivation of the inner surface of a glass or fused silica capillary tube prior to coating with stationary phase is obtained by a multi-step process whereby siloxane polymer molecules are chemically bonded to the capillary inner surface. The process comprises multiple cycles of successive reactions with silicon tetrachloride and a diorganodichlorosilane vapor with intermediate hydrolyses and a final capping reaction with a triorganochlorosilane. The deactivated surface is adapted to coating with an apolar liquid stationary phase.

16 Claims, 2 Drawing Figures

COATED CAPILLARY CHROMATOGRAPHIC COLUMN

FIELD OF THE INVENTION

The present invention relates to chromatographic column capillaries of the wall coated open tubular (WCOT) type in which the stationary liquid phase is present as a thin film supported by the inner surface of the capillary. More specifically, the present invention relates to glass and fused silica capillaries having an inactivated inner surface prepared by chemically bonding to the glass or silica surface an essentially chromatographically inactive, thin film of siloxane polymer molecules; and upon which bonded film layer is applied an apolar polymer coating as the stationary liquid phase.

BACKGROUND OF THE INVENTION

Regardless of glass capillary composition (most frequently soft or borosilicate glass, or fused silica), elimination of surface active sites is fundamentally important if maximum efficiency and applicability are to be achieved in the finished column. In this respect, the prior art has only been partly successful in developing satisfactory deactivation procedures, and the procedures which have been developed are often narrowly limited in success.

Probably the most widely applied of the prior art methods of capillary surface deactivation are those processes involving acid leaching the capillary inner surface which increases the density of the surface hydroxyl groups. This is followed by reacting the acid-leached surface with silylating reagents, commonly methylchlorosilanes, whereby the active hydroxyl groups are replaced by inert silyl-ether groups. Generally high reactive temperatures are required for proper silylation (e.g., about 400° C. or greater). In addition, the selection of the silylating reagent, its concentration, distribution in the capillary column, temperature and time are all highly critical parameters in these prior art processes, as described by Godefroot et al., Journal of HRC and CC, Vol. 3, July 1980, pp. 337-344). Despite strictest adherence to process variable control, Godefroot et al. observed difficulty with these procedures in reproducing uniform capillary columns, and caution that the results which are obtained are to be treated as strictly limited. Grob et al., Journal of HRC and CC, Vol. 3, April, 1980, pp. 197, 198, similarly observe that high temperature silylation surface deactivation is difficult to control and described the processes in terms of results as achieving only limited success. Nevertheless, Grob et al. judge the current high temperature silylating procedures, despite the serious limitations reported as being "the most efficient way (known) to produce very inert columns."

The invention in response to these problems provides improved glass and fused silica capillaries in which highly improved surface deactivation results are produced by bonding to the glass or silica a thin, inactive surface film of siloxane polymer molecules. Used in conjunction with apolar polymer film coatings, capillaries prepared by this new procedure demonstrate significantly lower residual surface activities than their commercially available counterparts, have much improved thermal stability, and are reasonably simple to reproducibly prepare via safe laboratory practices.

BRIEF SUMMARY OF THE INVENTION

It has now been discovered that improved chromatographic column capillaries of the wall coated open tubular type, and having as the liquid stationary phase, an apolar polymer film coating supported by the inner surface of the capillary, may be prepared by providing as the deactivated surface on which the liquid phase is deposited, a thin low activity film of siloxane polymer molecules. Chromatographic column capillaries prepared in this manner have unusually beneficial chromatographic properties namely, the combination of low activity, high attainable capacity, and long column life due to excellent thermal stability.

Specifically, the chromatographic column capillaries of the invention are prepared from glass capillary tubes, the inner surface of which is etched and acid-activated, or fused silica capillary tubes, the inner surface of which is acid-activated, by:

(a) contacting the etched and/or acid-activated surface with $SiCl_4$ vapor, thereby causing substantial chlorosilylation of said surface, (b) contacting the chlorosilylated surface with water vapor until essentially all of the chlorosilyl groups have been hydrolyzed to hydroxysilyl groups, (c) contacting the hydrolyzed surface with excess of a diorganodichlorosilane vapor of the formula $RR'SiCl_2$ where $RR'$ each represent a methyl, ethyl, vinyl, or allyl radical or a mono-chlorinated derivative thereof, to react at least the major portion of the hydroxysilyl groups to form corresponding diorganochlorosilyl groups, (d) contacting the reacted surface from step (c) with water vapor until essentially all of the diorganochlorosilyl groups have been hydrolyzed to diorganohydroxysilyl groups, (e) contacting the hydrolyzed surface of step (d) with $SiCl_4$ vapor to react substantially all of said diorganohydroxysilyl groups to form diorganosilyloxychlorosilyl groups, (f) repeating steps b-d not less than once, and (g) contacting the final hydrolyzed surface from step (f) with a triorganochlorosilane vapor of the formula $RR'R'' SiCl$ where $RR'R''$ each represent a methyl, ethyl, vinyl, or allyl radical, or a mono-chlorinated derivative thereof, to convert substantially all diorganohydroxysilyl groups to corresponding triorganosilyloxydiorganosilyl groups.

Any of the individual reaction and hydrolysis steps may be repeated one or more times to obtain essentially complete reaction of the affected hydroxyl and chloro functional groups, using reaction temperatures within the range of generally from about 0°-300° C. After the series of dichlorosilane reaction-hydrolysis sequences and the final reaction with chlorosilane, the inner surface of the capillary tubing has been effectively deactivated by a covering of thin film of siloxane polymer molecules, each chemically bonded at one end of the capillary surface and the free ends capped by triorganosilyloxy terminal groups. After appropriate flushing and drying steps, the deactivated surface is then coated by conventional means with a film of an appropriate apolar liquid polymer between about 0.1 to 10 microns uniform thickness.

DRAWING

Yet further details and advantages of the improved chromatography column capillaries of the invention and process for preparing same are set forth in the following Detailed Description of the Invention, taken with the accompanying drawing, in which:

FIG. 1 illustrates a chromatogram developed using the improved chromatography column capillary of the invention for analysis of a sample of mixed phenols; and FIG. 2 is an illustration of another chromatogram developed using a modified version of the chromatography column capillary of the invention for the analysis of Aroclor ® 1242 (a sample matrix of mixed polychlorinated biphenyls).

DETAILED DESCRIPTION OF THE INVENTION

Figure 1:
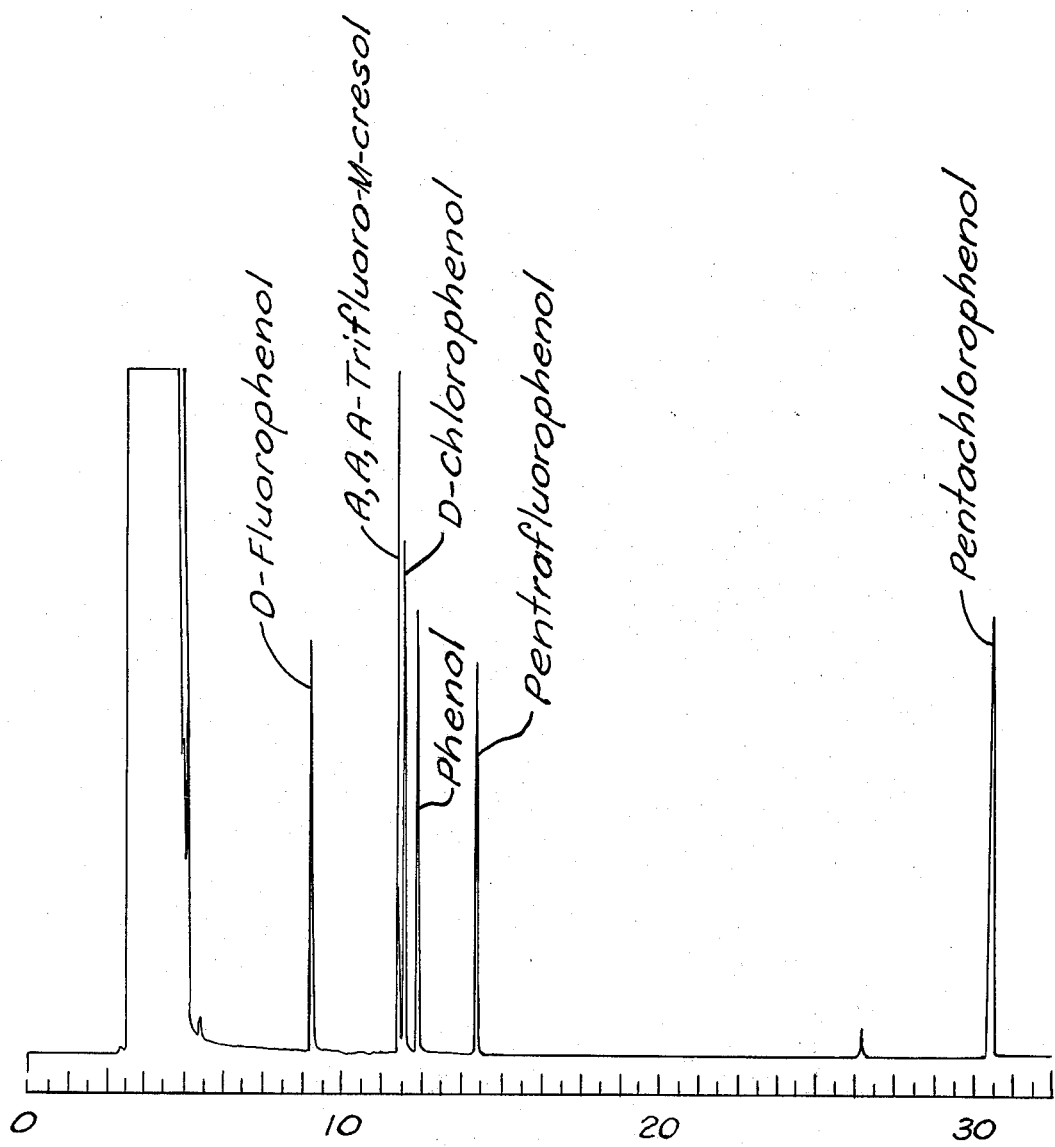

The inner column surface of a glass capillary tube is first etched by an acid fluoride solution as a preliminary step before the deactivation process. This can be done by a conventional treatment with aqueous 20% $KHF_2$ or by filling the column with saturated methanolic $NH_4HF_2$, allowing it to stand for an hour, then heating the emptied and dried column at 450° C. as described in the literature. For optimum uniform etching, however, a modification of the latter process is preferred. In this modified etching process, a saturated or essentially saturated solution of $NH_4HF_2$ in methanol is slowly passed through the column at about ambient temperature over a period of about 6–12 hours, the column is then rinsed with methanol to which there is gradually added an increasing proportion of water until the rinse becomes pure water, thereby removing the $(NH_4)_2SiF_6$ etching reaction product over a period of time and thus preventing plugging, and finally rinsing the column with methanol and drying. This latter and preferred etching process is the invention described and claimed in concurrently filed application Ser. No. 330,359, filed Dec. 14, 1981, by Peters, entitled "Process for Etching Glass Capillaries for Chromatography".

The etched glass column surface or fused silica surface is additionally, as a preparatory step, acid-activated by exhaustive treatment with concentrated aqueous hydrochloric acid at or near its boiling point for an extended period of time, for example, 24–48 hours. Such hot acid leaching is a known procedure that accomplishes the removal of undesirable cationic species such as $Na_2O$, $K_2O$, $Al_2O_3$, $B_2O_3$, $CaO$, and other metal oxides and that also produces an increased concentration of silanol groups, i.e., hydroxyl groups, bonded to the exposed silica surface. In this way, a more uniform coating of bonded siloxane polymer molecules on the silica surface is attainable by the series of reactions constituting the deactivation process and consequently a more thorough uniform deactivation of the surface is produced.

Hydrochloric acid leaching (acid-activation) is preferably followed by passing a stream of dry nitrogen through the tube to promote drying, while heating the capillary via, e.g., an infrared lamp, a known procedure referred to as "hydro-acidic thermal treatment". Hydro-acidic thermal treatment of the glass surface permits a beneficial increase in surface silanol density under generally reproducible conditions.

The surface silanol concentration is thereafter further increased substantially by step (a) of the above-described process wherein $SiCl_4$ vapor is contacted with the acid-activated silica surface, thereby causing reaction of the $SiCl_4$ with surface hydroxyl groups to make chlorosilyloxy moieties which are then converted to corresponding hydroxysilyloxy moieties by contact with water vapor in step (b). The reaction with $RR'SiCl_2$ vapor, the aqueous hydrolysis of the resulting disubstituted chlorosilyl end groups, the further branching reaction with $SiCl_4$ vapor and subsequent aqueous hydrolysis step then follow as set forth with the final capping reaction with $RR'R''SiCl$ to finish the siloxane polymer chain growth.

These reactions of the functional groups attached to the silica surface with vaporous reactants are preferably carried out by using an inert carrier gas such as nitrogen saturated with the vapor by bubbling it through the liquid chlorosilane or water. Optimum results are obtained by introducing the reactant vapor into the capillary tube at about room temperature and passing the vapor-gas mixture through for about 1–10 minutes, then flame-sealing the column ends and heating the sealed system for at least 0.1–0.2 hour at one or more temperatures in the range preferably from about 100° C. to 300° C. This procedure may be repeated about 1–3 times for each reaction step to assure as complete a reaction as possible before proceeding to the next step.

The final capping reaction with $RR'R''SiCl$ is preferably preceded by multiple hydrolyses with water vapor to insure complete hydrolysis of any residual chlorosilyl groups. Usually, about 3–5 such hydrolysis steps are found to be necessary before no traces of HCl can be detected when the hydrolyzed column is flushed with dry nitrogen. After treatment with $RR'R''SiCl$ vapor as specified above, the column is preferably flushed again with dry nitrogen or other inert gas and rinsed by passing through a low boiling inert solvent such as methylene chloride or pentane thereby dissolving and removing any unbonded siloxane polymer. The rinsed column is then flushed with nitrogen, subjected to a final hydrolysis step and a reaction with $RR'R''SiCl$ vapor as before to complete this preferred capping reaction procedure prior to coating the deactivated column surface with a liquid stationary phase.

Preferred end capping silanes of the formula $RR'R''SiCl$ include trimethylchlorosilane, (a highly preferred species), and additionally dimethylvinylchlorosilane, dimethylallylchlorosilane, and dimethylethylchlorosilane. Preferred reactants of the formula $RR'SiCl_2$ include dimethyldichlorosilane (a highly preferred species) and additionally methylvinyldichlorosilane, methylethyldichlorosilane, diethyldichlorosilane, and methylallyldichlorosilane. In addition, dichlorosilane and chlorosilane reactants broadly within the scope of the invention include those with organo methyl, ethyl, vinyl and allyl radicals, as described, including such radicals nondetrimental substituted with chlorine, as for example, methylchloromethyldichlorosilane and chloromethyldimethylchlorosilane.

Stationary Phase

The above-described deactivation procedure is specifically designed to provide optimum gas chromatographic properties in a column coated with an apolar stationary liquid phase. As a practical definition, "apolar" stationary phases have a value for the sum of the McReynolds' constants (*J. Chromatogr. Sci.*, 8, 685–691, 1970) for benzene, butanol, 2-pentanone, nitropropane, and pyridine of ~423 or less. The following list are examples of common apolar phases contemplated for use in the invention is given for illustrative purposes:

Squalane (hydrocarbon)
Nujol (hydrocarbon)
Hexatriacontane (hydrocarbon)

Kovat's Hydrocarbon
SF-96 (methyl silicone)
DC-330 (methyl silicone)
Convoil 20
M&B Oil (methyl silicone)
SE-30 (methyl silicone)
E-301 (methyl silicone)
UC-L46 (methyl silicone)
OV-1 (methyl silicone)
OV-101 (methyl silicone)
SE-31 (methyl silicone)
W-982 (methyl silicone)
DC-200 (methyl silicone)
SE-33 (methyl silicone)
SP-2100 (methyl silicone)
DC-11 (methyl silicone)
DC-410 (methyl silicone)
Montan Wax
Versilube F-50 (methyl, 10% trichlorophenyl silicone)
Polybutene 32 (hydrocarbon)
Polybutene 128 (hydrocarbon)
DC-510 (methyl silicone)
Apiezon M (hydrocarbon)
Apiezon L (hydrocarbon)
SE-52 (methyl, 5% phenyl silicone)
DC-560 (methyl, chlorophenyl silicone)
SP-400 (methyl, chlorophenyl silicone)
SE-54 (methyl, 1% vinyl, 5% phenyl silicone)
DC-556
Apiezon J (hydrocarbon)
Apiezon N (hydrocarbon)
Apiezon T (hydrocarbon)
Butyl stearate (hydrocarbon ester)
OV-3 (methyl, 10% phenyl silicone)

In many cases the defined surface deactivation procedure is compatible with mixed stationary phases, where the mixture may contain up to approximately 20 percent by weight of a more polar stationary phase in the primary apolar phase. Examples of such polar stationary phase components (illustrative only and not comprehensive) are:
Poly S-179 (polyphenylsulfone)
Poly S-176 (polyphenylsulfone)
Dexsil ® 400 (methyl phenyl carborane silicone)
Dexsil ® 410 (methyl cyanoethyl carborane silicone)
Poly MPE (polyphenyl ether)
PPE-20 (polyphenyl ether)
PPE-21 (polyphenyl ether)
BMBT (N,N'-bis(paramethoxybenzylidene)-a,a'-bi-para-toluidene)
BBBT (N,N'-bis(parabutoxybenzylidene)-a,a'-bi-para-toluidene)
BPhBT (N,N'-bis(paraphenylbenzylidene)-a,a'-bi-para-toluidene)

The apolar liquid coating is applied by conventional means. Preferably, the cooled and nitrogen-flushed column is filled with a solution of the coating in a low boiling inert solvent such as benzene, pentane, methylene chloride, or acetone and then evaporating the solvent. Stationary phase coatings of about 0.1–2 micron thickness are ordinarily preferred. The actual thickness of the chemically bonded methylsiloxane polymer deactivating film applied by the procedure of this invention is not known but is believed to be of the order of 0.01–0.1 percent of the thickness of the stationary phase film.

The deactivating procedure described herein is applicable to heat-resistant glass capillary columns conventionally used in gas chromatography. This includes capillaries of borosilicate glass, soft glass, and fused silica most generally of between about 0.1–0.8 mm I.D., and from about 10–100 meters in length.

EXAMPLE 1

Etching and Leaching Procedures

A glass capillary column of 0.40 mm I.D. and about 45 meters long was prepared by drawing commercially available Pyrex borosilicate tubing which had been rinsed with dilute aqueous hydrofluoric acid, deionized water, methanol, and methylene chloride, then air dried prior to drawing. The inside surface of the column was etched by pushing a saturated solution of $NH_4HF_2$ in methanol (about 4 percent by weight) through the column at about 25° C. and at a rate of about 1–10 ml/hr for 20 hours using nitrogen pressure. The column was then rinsed with about five times its volume of methanol (pumped through at 0.5–1 ml/min), water was introduced into the methanol feed in gradually increasing proportions via a 10 ml mixing vessel between the pump and column inlet until the rinse feed was pure water (about ten minutes) and the column was rinsed with five times its volume of water, and finally the column was rinsed again with methanol and dried with nitrogen.

The etched capillary column thereby obtained was leached by passing concentrated HCl through it at 1–10 ml/hr for about 24 hours at 60°–95° C. using an infrared lamp for heat. The column was then purged with dry nitrogen at 10 p.s.i. under the heat lamp until visually dry and the etched inside surface was deactivated according to the procedure described below. In the various steps, dry nitrogen was supplied at 10 p.s.i. and saturated at 25° C. with a reagent as necessary by using a bubbler bottle.

(1) Chlorosilylation

The column was filled with nitrogen saturated with $SiCl_4$ for about 3 minutes, then the ends were flame-sealed and the column was heated at 180° C. for about 30 minutes.

(2) Hydrolysis

The column was cooled to 25° C. and the sealed ends broken open to purge with dry $N_2$ for about 5 minutes, then with water-saturated $N_2$ for about 10 minutes. Then the ends were flame-sealed again and the column was heated ten minutes at 150° C.

(3) Reactions with Dimethyldichlorosilane (DMCS)

Nitrogen saturated with $(CH_3)_2SiCl_2$ vapor was passed through the cooled and opened column for 8 minutes, then water-saturated nitrogen was passed for 10 minutes, then $(CH_3)_2SiCl_2$-saturated nitrogen for 8 minutes. The column ends were then flame-sealed and the column was heated for 60 minutes at 180° C. The column was then cooled to 25° C. and the ends broken open. Nitrogen saturated with water vapor was passed through for 10 minutes, then nitrogen saturated with $(CH_3)_2SiCl_2$ for 5 minutes and finally water-saturated nitrogen for 10 minutes. The ends were flame-sealed and the column was heated at 180° C. for 10 minutes.

(4) Chlorosilylation and Hydrolysis

After cooling to 25° C., the column ends were broken open and the column was purged with nitrogen for ten minutes. Nitrogen saturated with $SiCl_4$ was passed through for 5 minutes, then the ends were flame-sealed and the column was heated at 180° C. for about 30 minutes. The column was again cooled to room temperature and purged with nitrogen for 5 minutes, then water-saturated nitrogen was passed through for 10 minutes, the column ends were sealed, and the column was heated for 10 minutes at 150° C.

(5) Reactions with Dimethyldichlorosilane (DMCS)

Nitrogen saturated with $(CH_3)_2SiCl_2$ vapor was passed through the cooled and opened column for 5 minutes, then water-saturated nitrogen was passed for 10 minutes, then $(CH_3)_2SiCl_2$-saturated nitrogen for 5 minutes. The column ends were then flame-sealed and the column was heated 10 minutes at 180° C. After cooling and opening, water-saturated nitrogen was passed through the column for 10 minutes, then $(CH_3)_2SiCl_2$-saturated nitrogen was passed for 5 minutes, and water-saturated nitrogen was passed for 10 minutes. The column ends were then flame-sealed and the column was heated 10 minutes at 180° C.

(6) Chlorosilylation and Hydrolysis

Step (4) was repeated except that the column was heated for 10 minutes at 180° C. after $SiCl_4$ vapor was passed and the ends were sealed.

(7) Reactions with $(CH_3)_2SiCl_2$ (DMCS)

Step (5) was repeated except that the final heating at 180° C. after the last passing of water-saturated nitrogen was continued overnight.

(8) Capping with Trimethylchlorosilane (TMCS)

The cooled and opened column was purged with dry nitrogen for 10 minutes, then nitrogen saturated with $(CH_3)_3SiCl$ vapor was passed through for 5 minutes, the ends were flame-sealed, and the column was heated at 200° C. for 10 minutes. The column was then cooled to room temperature, purged 10 minutes with nitrogen, and rinsed with two 5 ml portions of methylene chloride. After passing nitrogen to visual dryness, nitrogen saturated with $(CH_3)_3SiCl$ vapor was passed for 8 minutes, the ends of the column were flame-sealed, and the column was heated for 10 minutes at 180° C., then for 1 hour at 280° C.

(9) Static Coating

The cooled column was purged with dry nitrogen for about 30 minutes, then pressure filled with 0.35 volume percent OV-73 (a phenyl methyl silicone gum wherein the phenyl groups in the polymer molecule constituted 5.5 percent of the total organic substituents, manufactured by Ohio Valley Silicones) in pentane. One end of the column was sealed with glue and the other end was connected to a vacuum pump for vacuum evaporation of the pentane solvent while the body of the column was immersed in a water bath held at 33° C. When evaporation was completed, the column was installed in a gas chromatograph and conditioned by treatment overnight with helium at 250° C.

FIG. 1 shows the chromatogram of a sample of mixed phenols obtained by use of this column. Surface deactivation was excellent as the column efficiency approached the theoretical limit. The column length as used was 37 meters with a polysiloxane inner coating of 0.35 μm total thickness.

In the following example, the procedural steps described in Example 1 are indicated by an abbreviated notation. Thus, successive passage of $(CH_3)_2SiCl_2$ (DMCS)-saturated nitrogen, heating of the sealed and vapor-filled column at an elevated temperature, passage of wet nitrogen through the cooled column, and heating of the sealed and wet nitrogen-filled column are indicated as follows:

DMCS (10 min)→220° C. (2 hrs)

$H_2O$ (30 min)→220° C. (1 hr)

In all of these steps, as in Example 1, nitrogen at 10 pounds gauge pressure was bubbled through water or a chlorosilane and the saturated nitrogen stream was passed through the column at room temperature (about 25° C.), then the column ends were flame-sealed for the heating at an elevated temperature after which the column was cooled and the ends broken off for further treatments.

EXAMPLE 2

A borosilicate glass column of 0.60 mm inside diameter and about 35 meters long was made up, the inside surface etched with methanolic $NH_4HF_2$ and leached with hydrochloric acid as described in the above example. The dried column was then coated by the following combination of steps indicated by the notation used in Example 2.

(1) Chlorosilylation and Hydrolysis
$SiCl_4$ (5 min)→250° C. (2.5 hrs)
$N_2$ purge (10 min)
$H_2O$ (10 min)→150° C. (10 min)
$H_2O$ (10 min)→150° C. (10 min)

(2) Reactions with DMCS
DMCS (5 min)→150° C. (10 min)→250° C. (10 min)
$H_2O$ (10 min)→150° C. (10 min)
$H_2O$ (10 min)→150° C. (10 min)
DMCS (5 min)→150° C. (10 min)→250° C. (10 min)
$H_2O$ (10 min)→150° C. (10 min)
$H_2O$ (10 min)→150° C. (10 min)

(3) Chlorosilylation and Hydrolysis
$N_2$ purge (10 min)
$SiCl_4$ (5 min)→150° C. (10 min)→250° C. (10 min)
$N_2$ purge (10 min)
$H_2O$ (10 min)→150° C. (10 min)
$H_2O$ (10 min)→150° C. (10 min)

(4) Reactions with DMCS
DMCS (5 min)→150° C. (10 min)→250° C. (10 min)
$H_2O$ (10 min)→150° C. (10 min)
$H_2O$ (10 min)→150° C. (10 min)
DMCS (5 min)→150° C. (10 min)→250° C. (20 min)
$H_2O$ (10 min)→150° C. (10 min)
$H_2O$ (10 min)→150° C. (10 min)
$H_2O$ (10 min)→150° C. (10 min)
$H_2O$ (10 min)→150° C. (10 min)

(5) Capping with TMCS
$N_2$ purge (10 min)
TMCS (5 min)→150° C. (10 min)→250° C. (10 min)
$N_2$ purge (10 min)
One 7 ml $CH_2Cl_2$ rinse
$N_2$ purge until dry
$H_2O$ (10 min)→150° C. (10 min)→200° C. (10 min)
$N_2$ purge (10 min)
TMCS (5 min)→150° C. (10 min)→250° C. (30 min)
$N_2$ purge (10 min)

(6) Static Coating

The column was filled with a 0.27 percent by volume $CH_2Cl_2$ solution of a mixture of 9 parts by weight OV-73* to one part Poly S-179**. The pentane solvent was removed and the column conditioned in helium essentially as described in Example 1 to yield a column having a total polymer coating thickness of 0.40 micron.

* Polymer defined in Example 1.
** Polyphenylsulfone (Poly S-179)

Figure 2:
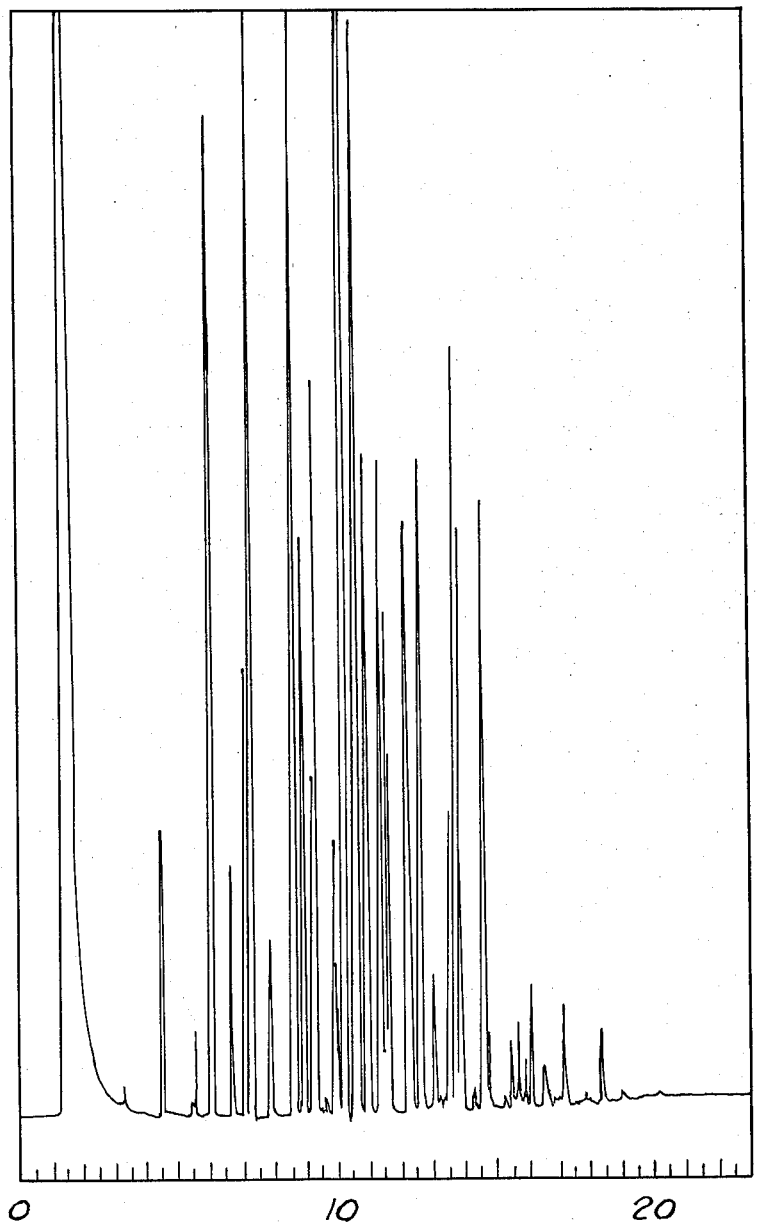

FIG. 2 shows the chromatogram of a sample of Aroclor 1242 (mixed polychlorinated biphenyls). Column length was about 27 meters.

What is claimed is:

1. In the process of preparing a chromatographic column using a glass capillary tube, the inner surface of which is etched and acid-activated, or fused silica capillary tube, the inner surface of which is acid-activated, the improved method of deactivating, the inner surface of the capillary which comprises:
   (a) contacting the etched and/or acid-activated surface with SiCl$_4$ vapor thereby causing substantial chlorosilylation of said surface,
   (b) contacting the chlorosilylated surface with water vapor until essentially all of the chlorosilyl groups have been hydrolyzed to hydroxysilyl groups,
   (c) contacting the hydrolyzed surface with excess of a diorganodichlorosilane vapor of the formula RR'SiCl$_2$ where RR' each represent a methyl, ethyl, vinyl, or allyl radical, or a mono-chlorinated derivative thereof, to react at least the major portion of the hydroxysilyl groups to form corresponding diorganochlorosilyl groups,
   (d) contacting the reacted surface from step (c) with water vapor until essentially all of the diorganochlorosilyl groups have been hydrolyzed to diorganohydroxysilyl groups,
   (e) contacting the hydrolyzed surface of step (d) with SiCl$_4$ vapor to react substantially all of said diorganohydroxysilyl groups to form diorganosilyloxychlorosilyl groups,
   (f) repeating steps b–d not less than once, and
   (g) contacting the final hydrolyzed surface from step (f) with a triorganochlorosilane vapor of the formula RR'R''SiCl where RR'R'' each represent a methyl, ethyl, vinyl or allyl radical, or a mono-chlorinated derivative thereof, to convert substantially all diorganohydroxysilyl groups to corresponding triorganosilyloxydiorganosilyl groups.

2. The process of claim 1 wherein the deactivated column surface is coated with a film of at least about 80 percent by weight apolar liquid polymer as a stationary phase.

3. The process of claim 2 wherein the apolar polymer is a methyl silicone.

4. The deactivated capillary column product of the process of claim 1.

5. An improved process for making a chromatographic separation comprising mixing the vapor of a substance having multiple components with an inert carrier gas and passing the gaseous mixture through the chromatographic column product of the process of claim 2.

6. The process of claim 5 wherein the chromatographic column is the product of the process of claim 3.

7. In an apparatus for use in chromatographic separations comprising a capillary glass or fused silica tube having a thin film of a stationary liquid phase supported by the inner surface of the tube, the improvement wherein the column is the product of the process of claim 2.

8. The apparatus of claim 7, the improvement wherein the column is the product of the process of claim 3.

9. In the process of preparing a chromatographic column of a glass capillary tube, the inner surface of which is etched and acid-activated or fused silica capillary tube, the inner surface of which is acid-activated, the improved method of deactivating the inner surface of the capillary which comprises:
   (a) contacting the etched and/or acid-activated surface with SiCl$_4$ vapor at about 0°–300° C., thereby causing substantial chlorosilylation of said surface,
   (b) contacting the chlorosilylated surface with water vapor at about 0°–300° C. until essentially all of the chlorosilyl groups have been hydrolyzed to hydroxysilyl groups,
   (c) contacting the hydrolyzed surface with excess dimethyldichlorosilane vapor at about 0°–300° C. for a time sufficient to react at least the major portion of the hydroxysilyl groups to form corresponding dimethylchlorosilyl groups,
   (d) contacting the reacted surface from step (c) with water vapor at about 0°–300° C. until essentially all of the dimethylchlorosilyl groups have been hydrolyzed to dimethylhydroxysilyl groups,
   (e) contacting the hydrolyzed surface from step (d) with SiCl$_4$ vapor at about 0°–300° C. for a time sufficient to react substantially all of said dimethylhydroxysilyl groups to form dimethylsilyloxychlorisilyl groups,
   (f) repeating steps b–d not less than once, and
   (g) contacting the final hydrolyzed surface from step (f) with trimethylchlorosilane vapor at about 0°–300° C. for a time sufficient to convert substantially all dimethylhydroxysilyl groups to corresponding trimethylsilyloxydimethylsilyl groups.

10. The process of claim 9 wherein the deactivated column surface is coated with a film of at least about 80 percent by weight of an apolar liquid polymer as a stationary phase.

11. The process of claim 10 wherein the apolar polymer is a methyl silicone polymer.

12. The deactivated capillary column product of the process of claim 9.

13. An improved process for making a chromatographic separation comprising mixing the vapor of a substance having multiple components with an inert carrier gas and passing the gaseous mixture through the chromatographic column product of the process of claim 10.

14. The process of claim 13 wherein the chromatographic column is the product of the process of claim 11.

15. In an apparatus for use in chromatographic separations comprising a capillary glass or fused silica tube having a thin film of a stationary liquid phase supported by the inner surface of the tube, the improvement wherein the column is the product of the process of claim 10.

16. The apparatus of claim 15, the improvement wherein the column is the product of the process of claim 11.

* * * * *